United States Patent [19]

Pong

[11] Patent Number: 4,822,629
[45] Date of Patent: Apr. 18, 1989

[54] AZUMOLENE DOSAGE FORM
[75] Inventor: Schwe F. Pong, Norwich, N.Y.
[73] Assignee: Norwich Eaton Pharmaceuticals, Inc., Norwich, N.Y.
[21] Appl. No.: 940,815
[22] Filed: Dec. 12, 1986
[51] Int. Cl.$^4$ .......................... A61K 9/32; A61K 9/36; A61K 9/58; A61K 9/62
[52] U.S. Cl. .................................. 424/480; 424/482; 514/390
[58] Field of Search .................. 514/390; 424/480, 482
[56] References Cited

U.S. PATENT DOCUMENTS

| | | | |
|---|---|---|---|
| 3,689,654 | 9/1972 | Conklin et al. | 514/390 |
| 4,049,650 | 9/1977 | White, Jr. | 542/400 |
| 4,369,172 | 1/1983 | Schor et al. | 424/430 |
| 4,370,313 | 1/1983 | Davies | 424/32 |
| 4,457,907 | 7/1984 | Porter | 424/482 |
| 4,543,359 | 9/1985 | Ellis et al. | 514/390 |
| 4,590,062 | 5/1986 | Jang | 424/469 |
| 4,644,031 | 2/1987 | Lehmann et al. | 524/501 |

Primary Examiner—Shep K. Rose
Attorney, Agent, or Firm—Milton B. Graff, IV; David L. Suter; Jack D. Schaeffer

[57] ABSTRACT

The invention involves a method for achieving systemic administration of azumolene by delivering the drug to the intestines without exposing the drug in the stomach, and pharmaceutical compositions for achieving such administration of azumolene.

19 Claims, No Drawings

AZUMOLENE DOSAGE FORM

TECHNICAL FIELD

This invention is concerned with a method of administering azumolene in order to achieve enhanced systemic absorption of the drug. More particularly, it is concerned with methods and means for dosing azumolene which protect it from exposure to a gastric environment.

BACKGROUND OF THE INVENTION

Azumolene is 1-[[[5-(4-bromophenyl)-2-oxazolyl]methylene]amino]-2,4-imidazolidinedione which is disclosed to be useful as a muscle relaxant in U.S. Pat. No. 4,049,650 issued to White on Sept. 20, 1977, the disclosure of which is hereby incorporated by reference. Example V of U.S. Pat. No. 4,049,650 discloses a method for preparing azumolene.

Dantrolene, 1-[[[5-(4-nitrophenyl)-2-furanyl]methylene]amino]-2,4-imidazolidinedione, has a chemical structure related to that of azumolene, and the sodium salt of dantrolene is commercially available as a muscle relaxant drug; see *Physicians Desk Reference,* 40th Edition (1986), E. R. Barnhart (Pub.), Medical Economics Company, Inc., pp. 1273–1275. Dantrolene sodium is commercially available in two forms, as an injectable, intravenous solution, and as capsules for oral administration. Commercial dantrolene sodium capsules comprise a mixture of dantrolene sodium, lactose, starch, talc, magnesium stearate and other minor ingredients contained in standard hard gelatin capsule shells; such dantrolene sodium capsules are disclosed in U.S. Pat. No. 3,689,654 issued to Conklin & D'Orazio on Sept. 5, 1972.

SUMMARY OF THE INVENTION

It is an object of the present invention to provide methods for achieving enhanced systemic absorption of azumolene from the gastrointestinal tract.

It is also an object of the present invention to provide dosage unit forms of azumolene which will achieve such enhanced systemic absorption.

The present invention involves a method of achieving systemic absorption of azumolene from the gastrointestinal tract of a human or lower mammal comprising delivering azumolene to the intestines without exposure of the azumolene in the stomach.

DETAILED DESCRIPTION OF THE INVENTION

Azumolene is known to have pharmacological activity as a muscle relaxant. As used herein, "azumolene" means 1-[[[5-(4-bromophenyl)-2-oxazolyl]methylene]amino]-2,4-im or a pharmaceutically acceptable salt or hydrate hereof. A preferred form of azumolene for achieving muscle relaxant activity upon administration to mammals is the monosodium salt of azumolene. As used herein, "azumolene sodium" means the monosodium salt of azumolene or a hydrate thereof. An especially preferred form of azumolene is the dihydrate of azumolene sodium:

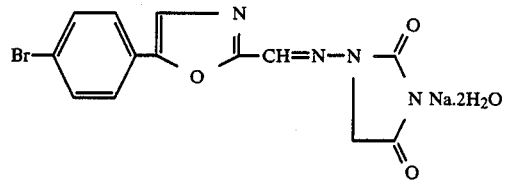

Azumolene and dantrolene are both muscle relaxants which act directly on skeletal muscles. In dantrolene sodium capsules, the dantrolene sodium is not coated. Upon oral ingestion of the capsules, the dantrolene is largely absorbed into the systemic system; very little is excreted in the feces. Good pharmacological activity results from such oral ingestion of dantrolene sodium. Based on the similar activities and chemical structures of dantrolene and azumolene, it was expected that upon oral ingestion of azumolene sodium, azumolene would be well absorbed into the systemic system and good pharmacological activity would result. However, the muscle relaxant activity achieved after oral ingestion of unprotected azumolene sodium is poor and inconsistent. It has been found that poor systemic absorption results from such oral ingestion of azumolene sodium. When a dose of azumolene sodium is ingested orally, it has been found that a substantial portion of the azumolene is excreted in the feces.

The present invention involves a method for delivering azumolene to the intestines without exposing the drug to the gastric environment of the stomach. It has been unexpectedly found that such a method of dosing azumolene sodium results in substantially greater systemic absorption of the drug, particularly in humans. The site of initial exposure of azumolene to a gastrointestinal environment is preferably in the small intestine, more preferably in the duodenum. As used herein, "exposure" means contact of the azumolene with the contents (juices and other materials) of the gastrointestinal tract (or the particular portion thereof which is specified), and that the azumolene is not separated from such gastrointestinal contents by a coating material or other barrier.

The method of dosing azumolene of the the present invention can be achieved, for example, by delivering a liquid solution, suspension, or emulsion of azumolene through a tube directly into the intestines. Such delivery via a tube through the oral or nasal cavity, esophagus and stomach into the intestines is well known. Alternatively, such liquid compositions of azumolene can be injected via a hypodermic needle directly into the intestines.

Another aspect of the present invention is a pharmaceutical composition comprising azumolene and means for delivering the azumolene to the intestines, preferably the small intestine, more preferably the duodenum, of a human or lower mammal, preferably a human, without exposing the azumolene in the stomach. Such compositions preferably comprise azumolene and a physiologically acceptable pharmaceutical carrier. As used herein, the term "pharmaceutical carrier" denotes a compatible solid or liquid filler, diluent, or encapsulating substance. By "compatible" as used herein, it is meant that the components are capable of being commingled without interacting in a manner which would substantially decrease the pharmaceutical efficacy of the dosage unit form of azumolene under ordinary use situations.

Some examples of substances which can serve as components of pharmaceutical carriers are sugars, such as lactose, glucose and sucrose; starches, such as corn starch and potato starch; cellulose and its derivatives, such as sodium carboxymethylcellulose, ethyl cellulose, and cellulose acetate; powdered tragacanth; malt; gelatin; talc; stearic acid; magnesium stearate; zinc stearate; calcium sulphate; silicon dioxide; vegetable oils, such as peanut oil, cottonseed oil, sesame oil, olive oil, corn oil and oil of theobroma; polyols, such as propylene glycol, glycerine, sorbitol, mannitol, and polyethylene glycol; agar; alginic acid; pyrogen-free water; isotonic saline; phosphate buffer solutions; organic solvents; wetting agents, surfactants and lubricants, such as sodium lauryl sulphate; coloring agents; flavoring agents; excipients; stabilizers; antioxidants; and preservatives; as well as other non-toxic compatible substances used in pharmaceutical formulations.

The pharmaceutical carrier employed in conjunction with azumolene in a pharmaceutical composition of the present invention is used at a concentration sufficient to provide a practical quantity-to-dosage relationship in the composition. Preferably, the pharmaceutical carrier comprises from about 0.1% to about 99% by weight of the total composition.

A preferred composition of the present invention is a dosage unit form for oral ingestion by a human or lower mammal comprising azumolene and means for protecting the azumolene from exposure while it is in the stomach, for delivering the azumolene to the intestines, preferably the small intestine, more preferably the duodenum, and for exposing the azumolene therein, whereby the azumolene is absorbed into the blood stream. Preferred dosage unit forms include those having an enteric release material surrounding the azumolene. As used herein, "enteric release material" means a material that will disintegrate or dissolve in environs typical of the intestines of a human or lower mammal, preferably of a human, but not in the environs typical of the stomach. Examples of enteric release materials are pH-sensitive polymers which provide an aqueous barrier and do not dissolve or disintegrate in acidic aqueous environs typical of the stomach, but which do dissolve or disintegrate in the higher pH aqueous environs typical of the intestines.

Preferred dosage unit forms of the present invention include enteric coated capsules or tablets, or enteric coated granules of azumolene, preferably azumolene sodium. Other preferred dosage unit forms include azumolene, preferably azumolene sodium encased in hard- or soft-shelled capsules with the shell made of an enteric release material. Another preferred dosage unit form provides azumolene, preferably azumolene sodium, embedded in a matrix which is soluble or erodible in the intestines but not in the stomach.

For the pharmaceutical compositions in dosage unit form of the present invention, each dosage unit form preferably contains from about 1 mg to about 1000 mg of azumolene, more preferably from about 10 mg to about 500 mg of azumolene, more preferably still from about 50 mg to about 200 mg of azumolene.

A preferred dosage unit form of the present invention is an enteric coated tablet comprising a tablet core containing azumolene surrounded by an enteric coating. Tablet cores area typically made by mixing granular or powdered azumolene with a pharmaceutical carrier and compressing the resulting mixture into a tablet core by conventional means. The tablet core is then coated with an enteric release material by conventional means, such as in a pan coater or a fluidized bed coater. Examples of commercially available enteric release materials which may be used to produce dosage unit forms of the present invention include methacrylic acid copolymers (Eudragit® L, S and L30D from Rohm Pharma GmbH, Darmstadt, West Germany); cellulose acetate phthalate (Aquateric® from FMC Corp., Philadelphia, PA); polyvinyl acetate phthalate (Coteric® from Colorcon Inc., West Point, PA); and hydroxypropyl methylcellulose phthalate (HP50 and HP55 from Shin-Etsu Chemical Co., Ltd., Tokyo, Japan). The preferred thickness of enteric coating used is sufficient to protect the azumolene from exposure in the stomach but disintegrates rapidly in the intestines, preferably in the small intestine, more preferably in the duodenum, to expose the azumolene, such that it can be absorbed from the intestines into the blood stream.

Another preferred dosage unit form of the present invention is an enteric coated hard gelatin capsule containing azumolene. Azumolene powder or granules are typically mixed with a pharmaceutical carrier and filled into hard gelatin capsule shells. The capsules are then enteric coated using a coating as described for enteric coated tablets above.

Another preferred dosage unit form of the present invention is enteric coated granules of azumolene. Granules comprising azumolene and, preferably, a pharmaceutical carrier are prepared and enterically coated using an enteric coating material as described hereinabove. A dosage unit form of the enteric coated granules is prepared by, preferably blending them with an appropriate pharmaceutical carrier, and compressing them into tablets or filling them into hard gelatin capsule shells by conventional means.

Another preferred dosage unit form of the present invention is a soft gelatin capsule containing a solution, suspension or emulsion of azumolene. The soft gelatin capsule shell is made of an enteric release material which remains intact in the stomach and prevents exposure of the azumolene in the stomach, but which dissolves or disintegrates in the intestines and releases the azumolene such that it can be absorbed from the intestines into the blood stream.

The following non-limiting examples provide typical formulations for dosage unit forms of the present invention.

EXAMPLE 1

Enteric coated tablets of azumolene sodium are produced using the following formulation:

| Ingredients | Weight Per Tablet (mg) |
| --- | --- |
| Tablet core | |
| Azumolene sodium | 100.0 |
| Lactose, anhydrous | 151.6 |
| Tablet core | |
| Starch, pregelatinized | 50.8 |
| Croscarmellose sodium, type A | 16.0 |
| Magnesium stearate | 1.6 |
| Coating mixture (dry basis) | |
| Methacrylic acid copolymer, aqueous dispersion | 14.5 |
| Propylene glycol | 1.5 |

| Ingredients | Weight Per Tablet (mg) |
|---|---|
| Talc | 3.3 |

All of the tablet core ingredients, except for half of the magnesium stearate which is held separately, are uniformly blended in a conventional mixer. The blend is then densified in a roller compacter. The compacted blend is granulated through a coarse screen (e.g. 10 mesh U.S. sieve) and then returned to the mixer where the remainder of the magnesium stearate is incorporated into the blend. The resulting blend is compressed into tablet cores using conventional tableting equipment. The coating mixture ingredients are blended according to the instructions of the enteric coating manufacturer. The tablet cores are coated in a conventional pan coater or fluidized bed coater using an aqueous dispersion of the coating mixture.

EXAMPLE 2

Enteric coated granules of the present invention are prepared using the following formulation:

| Ingredients | Weight Per Dose (mg) |
|---|---|
| Granules mixture | |
| Azumolene sodium | 100.0 |
| Lactose, anhydrous | 151.65 |
| Starch pregelatinized | 50.75 |
| Croscarmellose, sodium, type A | 16.0 |
| Magnesium stearate | 0.8 |
| Coating mixture (dry basis) | |
| Methacrylic acid copolymer, aqueous dispersion | 59.35 |
| Propylene glycol | 6.14 |
| Talc | 13.51 |

The granules mixture ingredients are uniformly blended in a conventional mixer. The blend is densified in a roller compacter. The compacted blend is granulated through a coarse screen (e.g. 10 mesh U.S. sieve) onto a finer screen (e.g. 20 mesh U.S. sieve). The granules that pass through the fine screen are returned to the roller compacter for recompacting. The granules retained on the fine screen are transferred to a fluidized bed column for coating. The coating mixture ingredients are blended according to the enteric coating manufacturer's instructions. The granules are coated in the fluidized bed coater. The coated granules are mixed with an appropriate pharmaceutical carrier, if needed (e.g. to provide proper flow characteristics), and are filled into hard gelatin capsules to provide a dosage unit form. Alternatively, the coated granules can be blended with an appropriate pharmaceutical carrier, if needed for desired tablet characteristics, and compressed into tablets using conventional tableting equipment.

While particular embodiments of the present invention have been described, it will be obvious to those skilled in the art that various changes and modifications of the present invention can be made without departing from the spirit and scope of the invention. It is intended to cover, in the appended claims, all such modifications that are within the scope of this invention.

What is claimed is:

1. A method of achieving systemic absorption of azumolene from the gastrointestinal tract of a human or lower mammal comprising orally delivering a safe and effect amount of azumolene to the intestines of said human or lower mammal without exposure of said azumolene in the stomach of said human or lower mammal.

2. The method of claim 1 wherein said azumolene is azumolene sodium.

3. The method of claim 2 wherein said azumolene sodium is initially exposed to a gastrointestinal environment in the duodenum following administration to a human.

4. A pharmaceutical composition comprising a safe and effective amount of azumolene and a means for orally delivering said azumolene to the intestines of a human or lower mammal without exposing said azumolene in the stomach of said human or lower mammal.

5. the composition of claim 4 wherein said azumolene is azumolene sodium.

6. The composition of claim 19 wherein said dosage unit form comprises from about 1 mg to about 1000 mg of azumolene sodium.

7. the composition of claim 19 wherein said dosage unit form is a soft gelatin capsule comprising a liquid solution, suspension or emulsion of azumolene sodium and a shell comprising an enteric release material.

8. The composition of claim 6 wherein said protecting means causes said azumolene sodium to be initially exposed to a gastrointestinal environment in the small intestine upon oral ingestion by a human.

9. The composition of claim 8 wherein said protecting means is an enteric release material surrounding said azumolene sodium.

10. The composition of claim 6 wherein said protecting means causes said azumolene sodium to be initially exposed to a gastrointestinal environment in the duodenum upon oral ingestion by a human.

11. The composition of claim 10 wherein said protecting means is an enteric release material surrounding said azumolene sodium.

12. A pharmaceutical composition in dosage unit form for oral ingestion comprising:
(a) from about 1 mg to about 1000 mg of azumolene, and
(b) enteric release material surrounding said azumolene.

13. The composition of claim 12 wherein said azumolene is azumolene sodium.

14. The composition of claim 13 wherein said composition comprises from about 10 mg to about 500 mg of azumolene sodium.

15. The composition of claim 13 wherein said composition comprises from about 50 mg to about 200 mg of azumolene sodium.

16. The composition of claim 14 wherein said dosage unit form is an enteric coated tablet.

17. the composition of claim 14 wherein said dosage unit form is an enteric coated capsule.

18. The composition of claim 14 wherein said dosage unit form comprises enteric coated azumolene sodium granules.

19. A pharmaceutical composition in unit dosage form for the oral administration of azumolene to a human or lower mammal, comprising: a safe and effective amount of azumolene; and a means for orally delivering said azumolene to the intestines of a human or lower mammal, whereby said azumolene is absorbed into the blood stream of said human or lower mammal; wherein said means protects said azumolene from exposure to gastric fluids while said unit dosage form is in the stomach of said human or lower mammal.

* * * * *